United States Patent
Zhang et al.

(10) Patent No.: US 11,143,496 B2
(45) Date of Patent: Oct. 12, 2021

(54) ELECTROSTATIC SELF-POWERED STRAIN GRID SENSOR

(71) Applicant: ZHEJIANG UNIVERSITY, Hangzhou (CN)

(72) Inventors: He Zhang, Hangzhou (CN); Liwei Quan, Hangzhou (CN); Jiwei Zhang, Hangzhou (CN); Zhicheng Zhang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/764,390

(22) PCT Filed: Jul. 25, 2019

(86) PCT No.: PCT/CN2019/097736
§ 371 (c)(1),
(2) Date: May 15, 2020

(87) PCT Pub. No.: WO2020/093735
PCT Pub. Date: May 14, 2020

(65) Prior Publication Data
US 2021/0270592 A1 Sep. 2, 2021

(30) Foreign Application Priority Data
Nov. 5, 2018 (CN) .......................... 201811308827.3

(51) Int. Cl.
*G01B 7/16* (2006.01)
*G01B 7/02* (2006.01)
*G01L 1/22* (2006.01)

(52) U.S. Cl.
CPC ................. *G01B 7/16* (2013.01); *G01B 7/02* (2013.01); *G01L 1/22* (2013.01); *G01L 1/2287* (2013.01); *A61B 2562/0261* (2013.01)

(58) Field of Classification Search
CPC .... G01B 7/16; G01B 7/20; G01B 7/02; G01L 1/2287; G01L 1/22; A61B 2562/0261
See application file for complete search history.

(56) References Cited

U.S. PATENT DOCUMENTS

2020/0393311 A1* 12/2020 Aizawa .................... G01B 7/16

FOREIGN PATENT DOCUMENTS

| CN | 86106558 A | 3/1988 |
| CN | 103791927 A | 5/2014 |

(Continued)

OTHER PUBLICATIONS

International Search Report (PCT/CN2019/097736); dated Sep. 26, 2019.

*Primary Examiner* — Amy He
(74) *Attorney, Agent, or Firm* — W&G Law Group

(57) ABSTRACT

The present disclosure provides an electrostatic self-powered strain grid sensor configured to measure strain of a component to be measured. The sensor includes a slide groove and a slide sheet. The slide groove is fixed to a fixing end and a sensor array is arranged at an inside bottom of the slide groove. The slide sheet is fixedly connected with the component to be measured and a lower end part of the slide sheet is in contact with the inside bottom of the slide groove. An electric signal is output when the slide sheet sweeps over the sensor array. Based on the output current of a sensor unit of the sensor array indicated by the signal, the number of segments swept over by the slide sheet and a distance swept over the sensor units in a single sensor array by the slide sheet is obtained, thereby acquiring a structural strain.

6 Claims, 2 Drawing Sheets

(56) References Cited

FOREIGN PATENT DOCUMENTS

| | | |
|---|---|---|
| CN | 108613623 A | 10/2018 |
| CN | 109458922 | 3/2019 |
| CN | 109470133 | 3/2019 |
| EP | 0522377 A | 1/1993 |

* cited by examiner

ELECTROSTATIC SELF-POWERED STRAIN GRID SENSOR

CROSS-REFERENCE TO RELATED APPLICATIONS

This application is a national stage of International Application No. PCT/CN2019/097736, filed on Jul. 25, 2019, which claims priority to Chinese Patent Application No. 201811308827.3, filed on Nov. 5, 2018. Both of the aforementioned applications are hereby incorporated by reference in their entireties.

TECHNICAL FIELD

The present disclosure relates to an electrostatic self-powered strain grid sensor.

BACKGROUND

A strain measurement for a structure is an important section for an engineer to optimize a structure design, to acquire a force receiving condition of the structure, and to ensure safety of the structure. In the current civil engineering industry, a strain measurement instrument is widely applied in measuring strain for bridges, railways, dams and various buildings. Commonly used strain measurement instruments at present mainly includes dial indicator strainmeters, resistance strainmeters, vibrating wire sensors, etc. Among these, if the dial indicator strainmeter is used to measure strain, there are many restrictions in practical application due to limitations of a marking length and installation; if the resistance strainmeter is used to measure strain, it has disadvantages of non-linearity, weak signal output, low anti-interference capability and being greatly affected by the environment, and it can only measure the strain of one point on a surface of a component along one direction rather than an overall measurement; and if the vibrating wire sensor is used to measure strain, requirements for a material and processing technology of the vibrating wire sensors is relatively high, and a measurement accuracy is relatively low.

SUMMARY

The technical problem to be solved by the present disclosure is to provide an electrostatic self-powered strain grid sensor capable of measuring strain without additional power supply and converting deformation energy of a to-be-measured component to electric energy and outputting the electric energy in forms of electric signals, electrostatic self-powered strain grid sensor having features of high accuracy, wide application, easy processing, low costs and simple operation.

A technical solution adopted to solve the technical problem in the present disclosure is to provide an electrostatic self-powered strain grid sensor configured to measure strain of a to-be-measured component. The electrostatic self-powered strain grid sensor includes a slide groove having a U shape, wherein a an upper end of the slide groove is opened to form an opening; a slide sheet is inserted in the opening, is parallel to a bottom surface of the slide groove, and has a same length as the bottom surface of the slide groove; a slide plate perpendicular to the slide sheet is fixed to a bottom surface of the slide sheet; and the slide plate is perpendicular to a direction along which the slide sheet slides; wherein one end of a top surface of the slide groove is fixed, via a connection component, to the component to be measured; a sensor array is arranged at the bottom surface of the slide groove and includes a plurality of sensor units each of which has a strip shape and each of which is parallel to the slide plate; and the slide sheet is inserted from another end of the slide groove, and an end of the slide sheet is fixed to the component to be measured; wherein a sensor unit having a strip shape is arranged at a lower end of the slide plate; the plurality of sensor units of the sensor array and the sensor unit arranged at the lower end of the slide plate each comprise a metal electrode layer and a dielectric material layer that are arranged in sequence; the dielectric material layer of each of the plurality of sensor units of the sensor array and the dielectric material layer of the sensor unit arranged at the lower end of the slide plate are in contact with each other and have opposite polarities; and after the metal electrode layer arranged at the lower end of the slide plate is connected to an ammeter, the metal electrode layer arranged at the lower end of the slide plate is connected to a plurality of indicator lights that is connected in parallel, and each of the plurality of indicator lights is connected to the metal electrode layer of one of the plurality of sensor units of the sensor array.

Further, the connection component is fixed, through an adhesive, to the component to be measured.

Further, the plurality of indicator lights and the ammeter are integrated on a back surface of the side groove.

Further, the slide groove, the slide sheet and the slide plate each are made of an insulating material.

Further, the plurality of sensor units of the sensor array has a same width, a distance between two adjacent sensor units of the plurality of sensor units is equal to the width of each of the plurality of sensor units, and a thickness of the slide plate is the same as the width of each of the plurality of sensor units.

Further, a strain value at a time t is calculated by a formula: $\varepsilon(t)=\Delta x(t)/l_1$, where $\Delta x(t)$ represents a displacement amount at the time t, and $l_1$ is a length of the slide groove; $\Delta x(t)=\Delta x_1(t)+\Delta x_2(t)$, where $\Delta x_1(t)=(|k|-1) \times l_0$, with k representing a sequence number of one of the plurality of indicator lights that is lighted up, and $l_0$ representing a sum of a width of each of the plurality of sensor units and a distance between two adjacent sensor units of the plurality of sensor units; and $\Delta x_2(t)=f(IR_k)$, with $R_k$ representing a resistance of a $k^{th}$ indicator light of the plurality of indicator lights, I a reading value of the ammeter, and f( ) is a function relational expression between an output voltage and a displacement between two adjacent sensor units.

The beneficial effects of the present disclosure are as below. In the present disclosure, when a component deforms under a strain, a force law of the component can be converted into an electrical signal according to a force-electricity conversion character of the component, the electrical signal passes through a signal processing device in the device, and the strain can be indicated by an electrical signal and output through an output device. Compared with other strain measurement devices, the electrostatic self-powered strain grid sensor has many advantages such as a simpler structure, wider applications, a higher measurement accuracy and no additional power supply, and creatively solves a problem of unstable result of strain indicated by an electric signal.

BRIEF DESCRIPTION OF DORIGINALINGS

Reference sign numbers: 1—slide groove; 2—slide sheet; 21—slide plate; 3—connection component; $l_0$—a sum of a width of one grid electrode on a sensor and a width of an adjacent segment to the grid electrode; $l_1$—an initial mark on the strain sensor; $\Delta x(t)$— amount of stretch/amount of compress of the component; $\Delta x_1(t)$—first displacement amount of the component; $\Delta x_2(t)$— second displacement amount of the component.

DESCRIPTION OF EMBODIMENTS

The specific technical solutions of the present disclosure will be further described below with reference to the drawings.

The present disclosure provides an electrostatic self-powered strain grid sensor configured to measure strain of a component to be measured and including a slide groove 1 having a U shape. An upper end of the slide groove 1 has an opening, and a slide sheet 2 is inserted in the opening. The slide sheet 2 is parallel to a bottom surface of the slide groove 1 and has a same length as the bottom surface of the slide groove 1. A slide plate 21 perpendicular to the slide sheet 2 is fixed to a bottom surface of the slide sheet 2. The slide plate 21 is perpendicular to a direction along which the slide sheet slides. One end of a top surface of the slide groove 1 is fixed, via a connection component 3, to the component to be measured. A sensor array is arranged at the bottom surface of the slide groove 1 and comprises sensor units each of which has a strip shape and each of which is parallel to the slide plate 21. The slide sheet 2 is inserted from another end of the slide groove 1, and an end of the slide sheet 2 is fixed to the component to be measured. A sensor unit having a strip shape is arranged at a lower end of the slide plate 21. The sensor units of the sensor array and the sensor unit arranged at the lower end of the slide plate each comprise a metal electrode layer and a dielectric material layer that are arranged in sequence. The dielectric material layer of each of the sensor units of the sensor array and the dielectric material layer of the sensor unit arranged at the lower end of the slide plate are in contact with each other and have opposite polarities. After the metal electrode layer arranged at the lower end of the slide plate 21 is connected to an ammeter, the metal electrode layer arranged at the lower end of the slide plate 21 is connected to indicator lights that are connected in parallel, and each of the indicator lights is connected to the metal electrode layer of one of sensor units of the sensor array.

Figure 1:
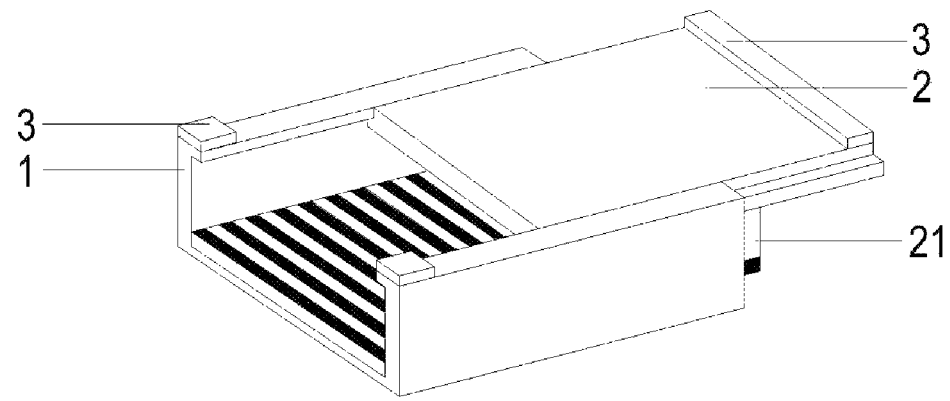
FIG. 1 is a schematic diagram of an electrostatic self-powered strain grid sensor.
Figure 2:
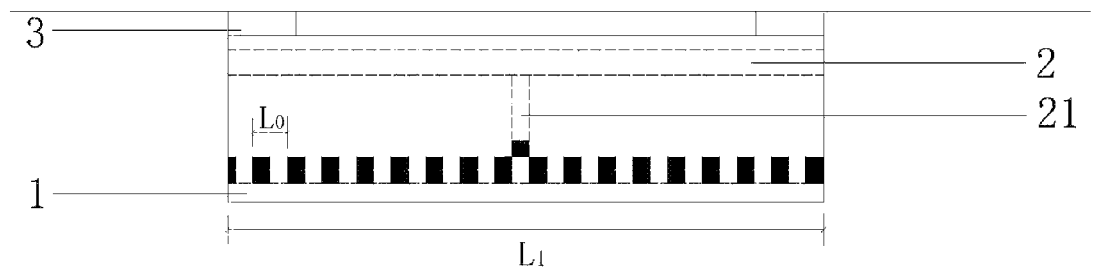
FIG. 2 is an installation diagram of a strain sensor arranged on a component a to be measured in FIG. 1.

The installation is as shown in FIG. 2 (a left end of the slide groove 1 is fixed to the component to be measured through the connection component 3 and a right end of the slide sheet is fixed to the component to be measured through the connection component 3). An electrical signal measurement device and related connection wires are integrated on a bottom of the side groove. The connection component is fixed to the component to be measured through an adhesive.

The sensor units of the sensor array have a same width, and a distance between two adjacent sensor units equals to the width of the sensor unit. A thickness of the slide plate is the same as the width of the sensor unit, which facilitates measurement.

The principle of an electrostatic self-powered strain grid sensor to measure strain in the present disclosure is as below.

Figure 5:
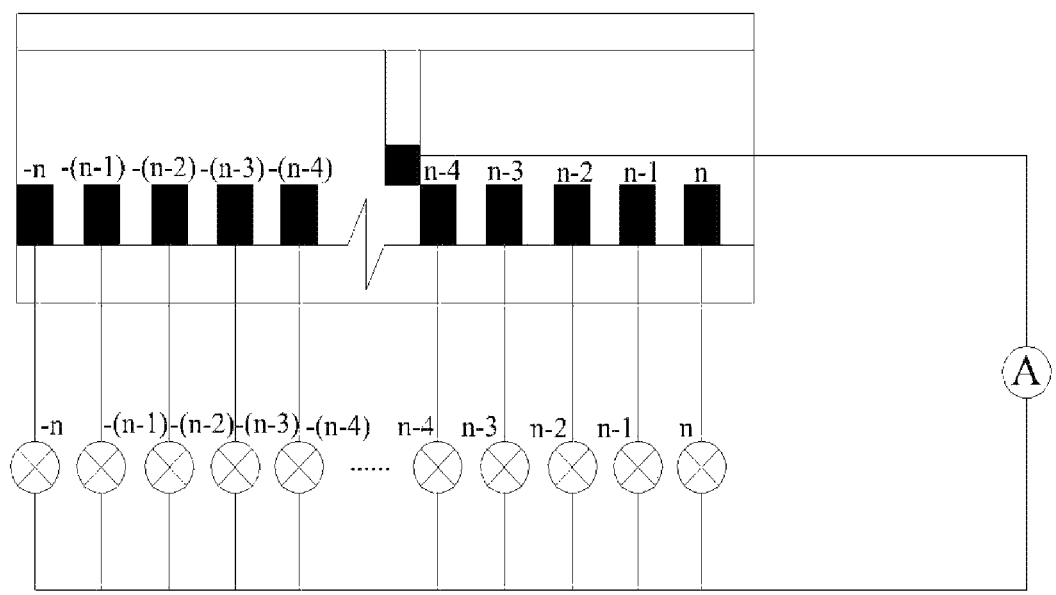
FIG. 5 is a circuit diagram of a displacement sensor for electrical signal measurement as shown in FIG. 1.

As shown in FIG. 5, each sensor unit of the sensor array of this structure is numbered, and sensor units of the sensor array are numbered from the middle to the two sides symmetrically. At a side facing away from a rectangular connection block arranged on the slide groove, the sensor units of the sensor array are numbered from 1 to n. At a side close to the rectangular connection block arranged on the slide groove, the sensor units of the sensor array are numbered from −1 to −n. Each sensor unit of the sensor array corresponds to one indicator light, and the number of the indicator light is the same as the sensor unit. The sensor unit arranged at the lower end of the slide sheet is connected to each sensor unit of the sensor array through a wire to form an indication circuit, and indication circuits are independent from each other and does not influence each other. The indication circuits are connected in parallel. Each circuit is provided with a corresponding indicator light. An ammeter is provided in a main circuit of a detection circuit. When the slide sheet sweeps over a $k^{th}$ sensor unit of the sensor array, one potential difference will be generated, and at this time the $k^{th}$ sensor unit and the sensor unit arranged at the lower end of the slide sheet can be regarded as a separate power supply through which power is supplied to light up a corresponding indicator light. If a length of $l_0$ is known, when the $k^{th}$ indicator light is lighted up, a first displacement amount of the component is $\Delta x_1(t)=(|k|-1)\times l_0$. That an indicator light with a negative number is lighted up indicates that an object to be measured is compressed. That an indicator lamp with a positive number is lighted up indicates that the object to be measured is stretched.

As described above, when the slide sheet sweeps over the $k^{th}$ sensor unit of the sensor array, I(t) will also be output. If a resistance of each indicator light is R is known, a voltage is calculated by $V(t)=R\times |I(t)|$. Moreover, according to a relational expression between V(t) and x(t) derived below, a second displacement amount $\Delta x_2(t)$ of the component can be acquired.

Figure 3:
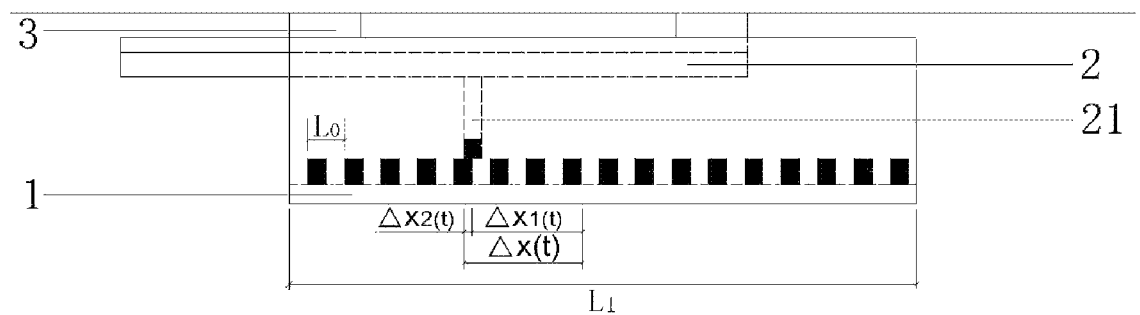
FIG. 3 is a schematic diagram illustrating a compression strain measurement state of an installation diagram as shown in FIG. 2.

Taking the object to be measured being in a compression strain measurement state illustrated in FIG. 3 as an example, a compression amount of the component is x(t) at one time t, that is, a relative displacement amount between a first electrode layer and a second electrode layer is x(t).

In the electrostatic self-powered strain grid sensor, thicknesses of the two kinds of dielectric materials are $d_1$ and $d_2$, respectively, and relative dielectric constants thereof are $\varepsilon_{r1}$ and gf $\varepsilon_{r2}$, respectively. The x(t) represents a relative displacement between electrode plates respectively coated by the two dielectric materials. When a displacement sensor device operates, x(t) changes from 0 to a maximum value. When there is no displacement between the electrode plates respectively coated by the two dielectric materials, i.e., x(t)=0, the electrode plates are charged, and surfaces of the two electrode plates respectively acquires opposite static charges and have equal charge densities a (charge density generated by contact friction). Moreover, when there is relative displacement between two electrode plates, charges generate a current through an external circuit. When a load resistance is set to be R, a charge amount Q can be expressed as:

$$R\frac{dQ(t)}{dt} = -\frac{d_0 Q(t)}{w\varepsilon_0(l-x(t))}, \quad (1)$$

Where $d_0 = d_1/\varepsilon_{r1} - d_2/\varepsilon_{r2}$, which is an equivalent thickness of k a dielectric material; l is a length of a dielectric material coating on an electrode plate; w is a width of a dielectric material on a single sensor unit; and $\varepsilon_0$ is a permittivity of vacuum.

Therefore, the voltage can be expressed as:

$$V(t) = -\frac{d_0 Q(t)}{w\varepsilon_0} + \frac{d_0 \sigma x(t)}{\varepsilon_0(l-x(t))} \quad (2)$$

By combining the two equations (1) and (2), a mapping relationship between the voltage V(t) and the displacement amount x(t) at the time t is obtained, that is, the displacement amount x(t) at the time t can be obtained by measuring the voltage V(t), thereby expressing the displacement amount as an electrical signal through a measurement circuit.

Figure 4:
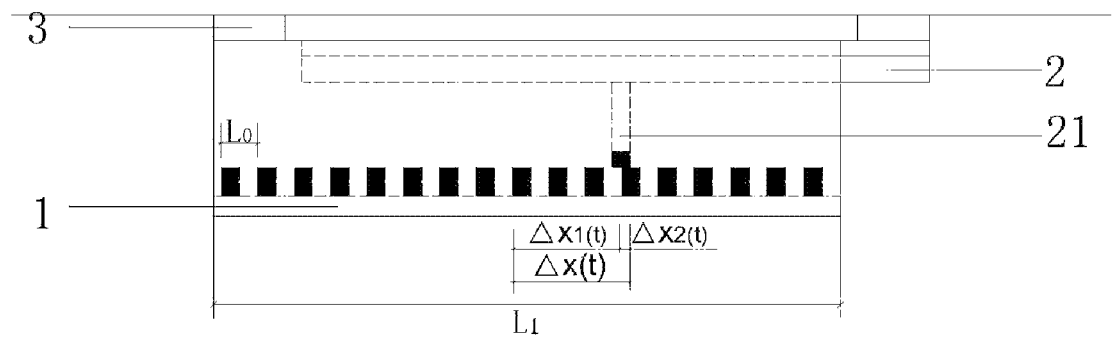
FIG. 4 is a schematic diagram illustrating a tensile strain measurement state of an installation diagram as shown in FIG. 2.

A principle of the object to be measured in a tensile strain measurement state as shown in FIG. 4 is the same as above.

In this case, a total displacement amount is obtained $\Delta x(t) = \Delta x_1(t) + \Delta x_2(t)$. When it is known that an initial mark of an initial strain sensor is $l_1$, a strain of the structure is $\varepsilon = \Delta x(t)/l_1$.

What is claimed is:

1. An electrostatic self-powered strain grid sensor configured to measure strain of a component to be measured, wherein the electrostatic self-powered strain grid sensor comprises:
    a slide groove (1) having a U shape, wherein an upper end of the slide groove (1) is opened to form an opening; a slide sheet (2) is inserted in the opening, is parallel to a bottom surface of the slide groove (1), and has a same length as the bottom surface of the slide groove (1); a slide plate (21) is fixed to a bottom surface of the slide sheet (2) and is perpendicular to the slide sheet (2); and the slide plate (21) is perpendicular to a direction along which the slide sheet slides;
    wherein one end of a top surface of the slide groove (1) is fixed, via a connection component (3), to the component to be measured; a sensor array is arranged at the bottom surface of the slide groove (1) and comprises a plurality of sensor units each of which has a strip shape and each of which is parallel to the slide plate (21); and the slide sheet (2) is inserted from another end of the slide groove (1), and an end of the slide sheet (2) is fixed to the component to be measured;
    wherein a sensor unit having a strip shape is arranged at a lower end of the slide plate (21); the plurality of sensor units of the sensor array and the sensor unit arranged at the lower end of the slide plate each are provided with both a metal electrode layer and a dielectric material layer in sequence; a dielectric material layer of each of the plurality of sensor units of the sensor array and a dielectric material layer of the sensor unit arranged at the lower end of the slide plate are in contact with each other and have opposite polarities; and after a metal electrode layer arranged at the lower end of the slide plate (21) is connected to an ammeter, the metal electrode layer arranged at the lower end of the slide plate (21) is connected to a plurality of indicator lights that is connected in parallel, and each of the plurality of indicator lights is connected to a metal electrode layer of one of the plurality of sensor units of the sensor array.

2. The sensor according to claim 1, wherein the connection component (3) is fixed, through an adhesive, to the component to be measured.

3. The sensor according to claim 1, wherein the plurality of indicator lights and the ammeter are integrated on a back surface of the side groove.

4. The sensor according to claim 1, wherein the slide groove, the slide sheet and the slide plate each are made of an insulating material.

5. The sensor according to claim 1, wherein the plurality of sensor units of the sensor array has a same width, a distance between two adjacent sensor units of the plurality of sensor units is equal to the width of each of the plurality of sensor units, and a thickness of the slide plate (21) is the same as the width of each of the plurality of sensor units.

6. The sensor according to claim 1, wherein a strain value at a time t is calculated by a formula: $\varepsilon(t) = \Delta x(t)/l_1$, where $\Delta x(t)$ represents a displacement amount at the time t, and $l_1$ is a length of the slide groove (1);
    wherein $\Delta x(t) = \Delta x_1(t) + \Delta x_2(t)$,
    wherein $\Delta x_1(t) = (|k|-1) \times l_0$, where k represents a sequence number of one of the plurality of indicator lights that is lighted up, and $l_0$ is a sum of a width of each of the plurality of sensor units and a distance between two adjacent sensor units of the plurality of sensor units; and
    wherein $\Delta x_2(t) = f(IR_k)$, where $R_k$ represents a resistance of a $k^{th}$ indicator light of the plurality of indicator lights, I represents a reading value of the ammeter, and f( ) is a function relational expression between an output voltage and a displacement between two adjacent sensor units.

* * * * *